(12) United States Patent
Beetel et al.

(10) Patent No.: US 8,386,010 B2
(45) Date of Patent: Feb. 26, 2013

(54) SURGICAL TISSUE MONITORING SYSTEM

(75) Inventors: Robert Beetel, Redwood City, CA (US);
Frank Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 281 days.

(21) Appl. No.: 12/572,156

(22) Filed: Oct. 1, 2009

(65) Prior Publication Data
US 2010/0137738 A1 Jun. 3, 2010

Related U.S. Application Data

(60) Provisional application No. 61/107,740, filed on Oct. 23, 2008.

(51) Int. Cl.
*A61B 5/04* (2006.01)
*A61B 5/0404* (2006.01)
*A61B 5/0408* (2006.01)
*A61B 5/042* (2006.01)
*A61B 5/05* (2006.01)
*A61B 5/053* (2006.01)

(52) U.S. Cl. ........ 600/393; 600/372; 600/373; 600/374; 600/547; 600/587; 606/41; 324/447; 324/448; 324/449

(58) Field of Classification Search .......... 600/372–374, 600/393, 547, 587; 606/41; 324/447–449
See application file for complete search history.

(56) References Cited

U.S. PATENT DOCUMENTS

| | | | |
|---|---|---|---|
| 4,304,239 A | 12/1981 | Perlin | |
| 4,836,214 A | 6/1989 | Sramek | |
| 4,852,580 A | 8/1989 | Wood | |
| 4,920,490 A | 4/1990 | Isaacson | |
| 5,010,894 A | 4/1991 | Edhag | |
| 5,056,532 A * | 10/1991 | Hull et al. | 607/124 |
| 5,117,828 A | 6/1992 | Metzger et al. | |
| 5,263,493 A | 11/1993 | Avitall | |
| 5,379,765 A | 1/1995 | Kajiwara et al. | |
| 5,454,377 A | 10/1995 | Dzwonczyk et al. | |
| 5,588,961 A * | 12/1996 | Leone et al. | 604/21 |
| 5,704,908 A * | 1/1998 | Hofmann et al. | 604/21 |
| 5,749,833 A | 5/1998 | Hakki et al. | |
| 5,807,272 A | 9/1998 | Kun et al. | |
| 5,860,974 A | 1/1999 | Abele | |
| 5,882,312 A | 3/1999 | Gopakumaran et al. | |
| 5,967,977 A | 10/1999 | Mullis et al. | |
| 6,122,544 A | 9/2000 | Organ | |
| 6,148,222 A * | 11/2000 | Ramsey, III | 600/380 |
| 6,292,689 B1 * | 9/2001 | Wallace et al. | 600/547 |
| 6,394,949 B1 * | 5/2002 | Crowley et al. | 600/127 |
| 6,501,984 B1 | 12/2002 | Church et al. | |
| 6,532,384 B1 | 3/2003 | Fukuda | |
| 6,584,348 B2 | 6/2003 | Glukhovsky | |
| 6,589,238 B2 | 7/2003 | Edwards et al. | |
| 6,640,120 B1 | 10/2003 | Swanson et al. | |
| 6,735,468 B2 | 5/2004 | Treppo et al. | |
| 6,813,515 B2 | 11/2004 | Hashimshony | |
| 6,882,879 B2 | 4/2005 | Rock | |
| 6,893,439 B2 | 5/2005 | Fleischman | |
| 6,932,812 B2 * | 8/2005 | Crowley et al. | 606/41 |
| 6,940,286 B2 | 9/2005 | Wang et al. | |
| 6,976,492 B2 * | 12/2005 | Ingle et al. | 128/898 |
| 7,184,811 B2 | 2/2007 | Phan et al. | |
| 7,770,584 B2 * | 8/2010 | Danek et al. | 128/898 |
| 7,947,038 B2 * | 5/2011 | Edwards | 606/41 |
| 8,032,222 B2 * | 10/2011 | Loushin et al. | 607/40 |

(Continued)

*Primary Examiner* — Sean Dougherty

(57) ABSTRACT

A tissue monitoring system includes an introducer having an inflatable section and a plurality of electrodes disposed thereon. The electrodes are alternatively connected to an electrode contact system which includes at least one signal line and at least one measurement line for taking readings about a circumferential segment of tissue encompassed by the electrodes.

9 Claims, 4 Drawing Sheets

U.S. PATENT DOCUMENTS

| | | |
|---|---|---|
| 2001/0051774 A1 | 12/2001 | Littrup et al. |
| 2003/0004434 A1 | 1/2003 | Greco et al. |
| 2003/0074039 A1* | 4/2003 | Puskas ................ 607/118 |
| 2003/0079753 A1* | 5/2003 | Vaska et al. ............ 128/898 |
| 2003/0088189 A1 | 5/2003 | Tu et al. |
| 2003/0105411 A1 | 6/2003 | Smallwood et al. |
| 2003/0216661 A1 | 11/2003 | Davies |
| 2004/0162501 A1 | 8/2004 | Imran |
| 2004/0210157 A1 | 10/2004 | Organ et al. |
| 2004/0230110 A1* | 11/2004 | Sinderby et al. ........ 600/393 |
| 2004/0230131 A1 | 11/2004 | Kassab et al. |
| 2005/0096647 A1* | 5/2005 | Steinke et al. ........... 606/41 |
| 2006/0004300 A1 | 1/2006 | Kennedy |
| 2006/0116564 A1 | 6/2006 | Mintchev et al. |
| 2006/0167374 A1 | 7/2006 | Takehara et al. |
| 2006/0200039 A1 | 9/2006 | Brockway et al. |
| 2007/0106292 A1* | 5/2007 | Kaplan et al. ........... 606/41 |
| 2007/0282187 A1* | 12/2007 | Long ..................... 600/372 |
| 2008/0103580 A1* | 5/2008 | Gerber .................... 607/149 |
| 2008/0161801 A1* | 7/2008 | Steinke et al. ........... 606/41 |
| 2008/0319504 A1* | 12/2008 | Loushin et al. ........... 607/40 |
| 2010/0094328 A1* | 4/2010 | O'dea et al. ............ 606/192 |

* cited by examiner

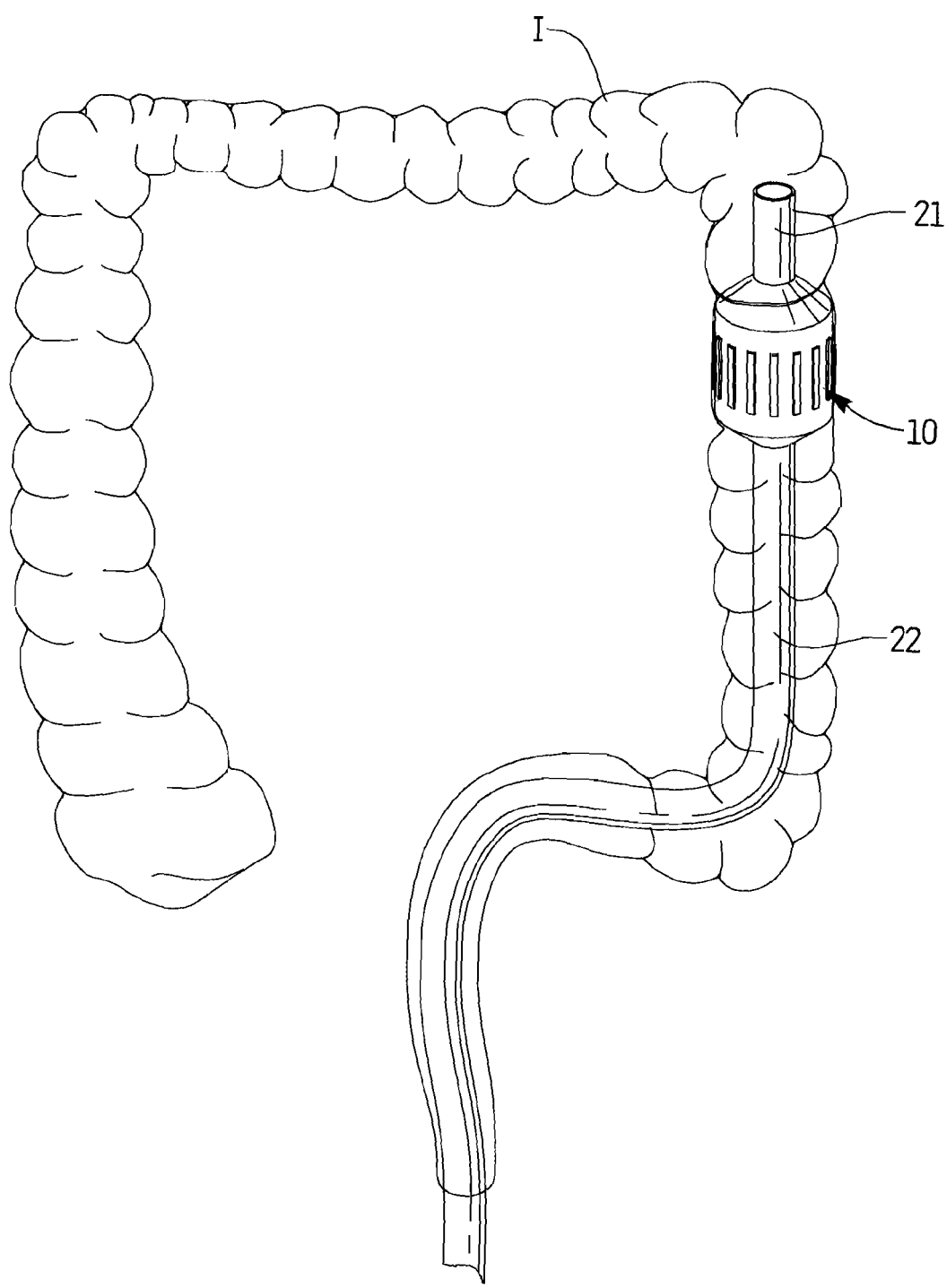

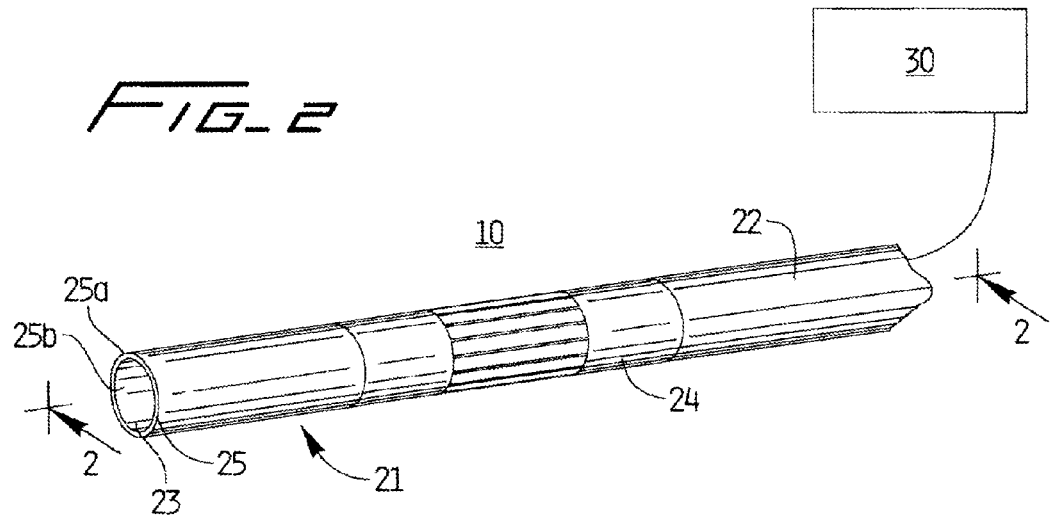
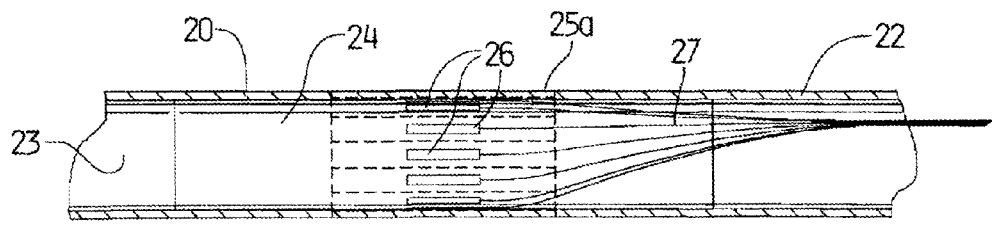
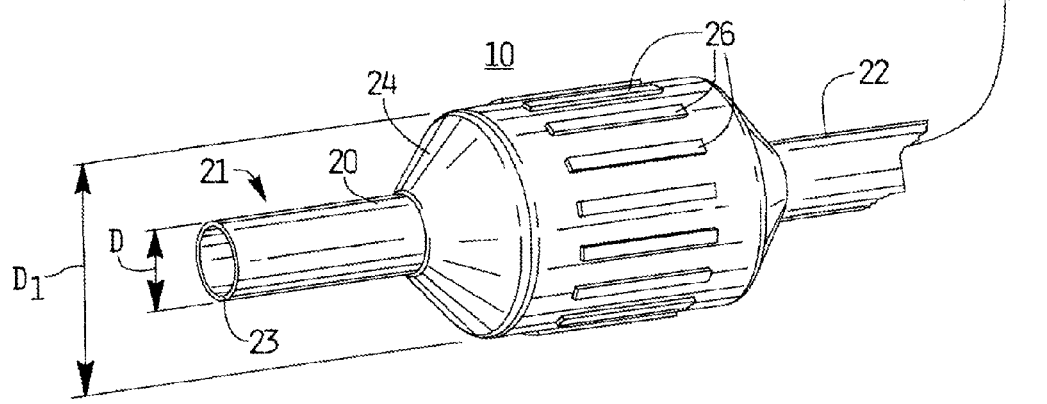

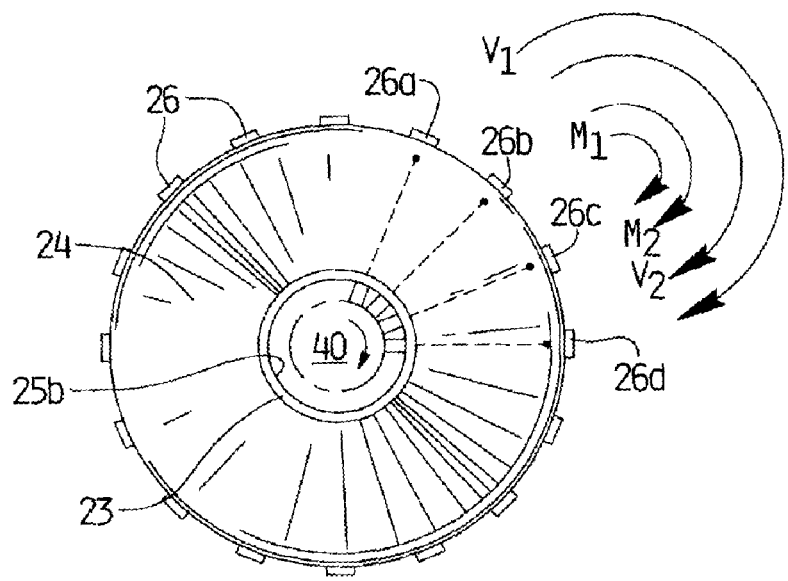
FIG_5
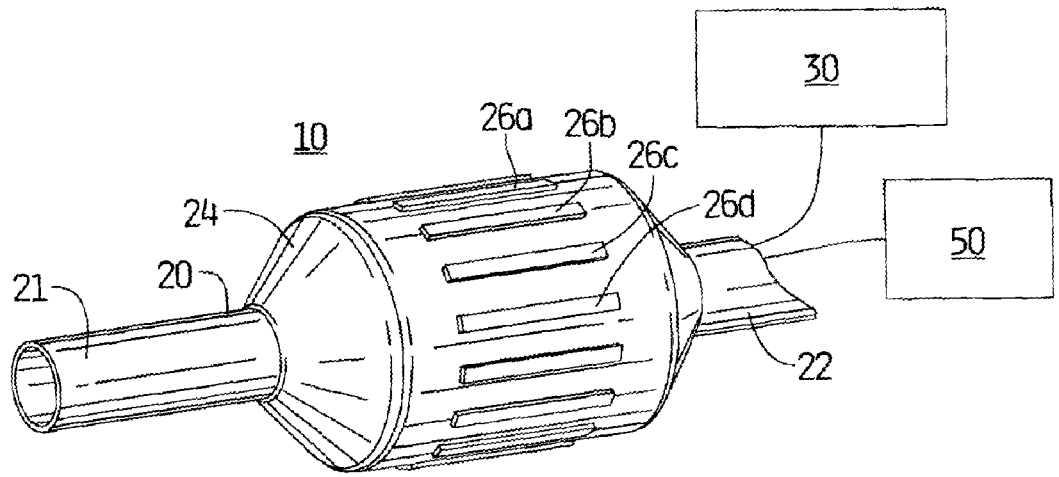
FIG_5A

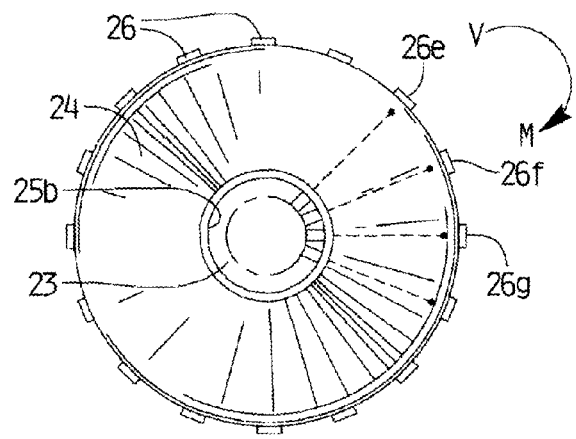
FIG_6
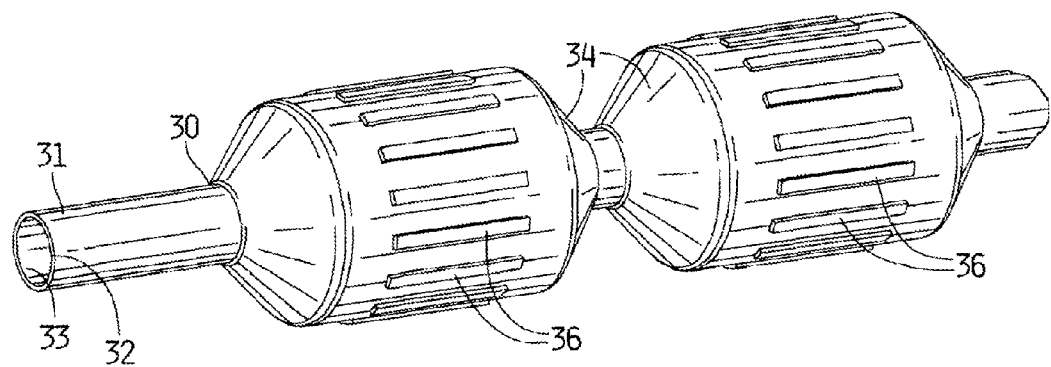
FIG_7

SURGICAL TISSUE MONITORING SYSTEM

The present application claims priority from U.S. Provisional Application No. 61/107,740, filed Oct. 23, 2008, the entire contents of which are incorporated herein by reference.

BACKGROUND

1. Technical Field

This invention relates generally to bioimpedance measuring systems and in particular to alternating electrode measuring systems for monitoring tissue.

2. Description of the Related Art

Tissue ischemia, a low oxygen state usually due to the obstruction of arterial blood supply or inadequate blood flow leading to hypoxia in tissue, has been widely reported as a cause of gastrointestinal anastomotic breakdown and leakage. Anastomotic leaks are especially prevalent and harmful in the esophagus and in the colon. Gastrointestinal tissue most vulnerable to ischemic conditions is the mucosal tissue on the surface of the intestinal lumen. The mucosal layer is the first tissue layer to show cell death and necrosis when perfusion is insufficient.

Impedance spectroscopy involves multiple measurements over a range of frequencies that provide information about the structural and electrical properties of a sample. Bioimpedance spectrum measurements involve measuring the electrical impedance of tissue to signals of different frequencies. Bioimpedance measurement systems use a number of different electrode configurations to measure tissue damage.

It would be advantageous to provide a system for monitoring the state of anastomosed tissue quickly, easily, and directly. The information provided would alert surgeons to conditions that precede or are associated with anastomotic breakdown and leakage. Having been alerted to impending complications, the surgeons could change their course of treatment to address the developing complication.

SUMMARY

The present disclosure is directed in one aspect towards a tissue monitoring system used to monitor post anastomotic perfusion along a staple line. The tissue monitoring device has an introducer having an inflatable section and a plurality of electrodes attached thereto. The electrodes are alternatively connected to an electrode contact measuring system having at least one signal line and at least one measurement line.

The introducer is placed proximal to a section of tissue and the inflatable section is preferably distended such that the plurality of electrodes disposed thereon is in contact with the tissue. Readings are taken about a circumferential segment of tissue encompassed by the electrodes.

In one embodiment, a four contact system is utilized to measure tissue impedance. In such four contact system, preferably four adjacent electrodes are arranged as two signal lines peripheral to (outboard of) two measurement lines. The electrodes of the two signal lines, or outer electrodes, impose an electrical signal on the tissue while the two electrodes of the measurement lines, or inner electrodes, measure the resulting potential. The spacing of the electrodes allows the voltage drop to be measured between the two inner electrodes as a result of the current at the outer two electrodes providing a reading that characterizes the impedance of the tissue.

In an alternate embodiment, a three contact system is utilized to measure tissue impedance. Three electrodes are arranged as a signal line, a measurement line, and a combined (common) signal and measurement line. The electrodes of the signal and measurement lines measure transfer impedance by imposing an electrical signal on the tissue with the signal electrode and measuring the resulting potential with the measurement electrode. The combined signal and measurement line electrode measures site impedance as it functions as both a signal and a measurement line.

The electrode contact system may be shifted by one or more electrodes to encompass a subset of electrodes that is adjacent to the electrode it was connected to previously in order to take readings and get information about the circumferential segment encompassed by the electrodes. The system may be shifted by mechanical or electrical controls. In one embodiment, the introducer has a rotating shaft for mechanical movement of the electrodes for alternating or sequencing placement of the electrodes. In other embodiments, the introducer has an external control, such as a commutator, to alternate the function of the electrodes by shifting each contact of the contact system.

BRIEF DESCRIPTION OF THE DRAWINGS

FIG. 1 is a perspective view of the tissue monitoring system of the present disclosure shown inserted into intestinal tissue.

FIG. 2 is a side plan view of the tissue monitoring system in accordance with a first embodiment of the present disclosure;

FIG. 3 is a side cross-sectional view of the introducer of the tissue monitoring system taken along line 2-2 of FIG. 2;

FIG. 4 is a side plan view of the tissue monitoring system of FIG. 2 in an inflated state;

FIG. 5 is a front elevation view of the tissue monitoring system of FIG. 1 having a rotating shaft and electrodes configured in a four contact system;

FIG. 5A is a side perspective view of an alternate embodiment of the tissue monitoring system of FIG. 5 having an external control;

FIG. 6 is a front elevation view of another embodiment of the tissue monitoring system having the electrodes configured in a three contact system; and FIG. 7 is a side perspective view of another alternate embodiment of the tissue monitoring system of the present disclosure having two inflatable sections.

DETAILED DESCRIPTION OF THE EMBODIMENTS

Referring now to the drawings, in which like reference numerals identify identical or substantially similar parts throughout the several views, FIG. 2 illustrates a side plan view of the tissue monitoring system in accordance with the principles of the present disclosure. Tissue monitoring system 10 includes introducer 20 and impedance spectrometer system 30.

Introducer 20 may be a catheter or scope or any other instrument capable of being inserted into the body with the intended purpose of accessing tissue. FIG. 1 illustrates the tissue monitoring system 10 positioned in intestinal tissue "T". Introducer 20 includes inflatable section 24 having a plurality of electrodes 26. Outer and inner walls 25a and 25b define an annular space for communicating distention fluid between a distention fluid source (not shown) and inflatable section 24. Inner wall 25b of introducer 20 also defines an internal longitudinal passage 23 which extends along the length of introducer 20 from the proximal end to the distal portion 21. The flexible region proximal of the inflatable section 24 is designated by reference numeral 22. Internal longitudinal passage 23 is dimensioned to permit passage of endoscopic instruments and other medical materials and substances therethrough.

Inflatable section 24 of introducer 20 may be of any length and preferably maintained adjacent distal section 21 of introducer 20. In the illustrated embodiment, inflatable section 24 is positioned in a distal section of the introducer 20, off-set from (proximal of) the distalmost end 25 of distal section 21. Inflatable section 24 includes a plurality of electrodes 26, preferably planar, although arcuate or other configurations are also contemplated. Electrodes 26 extend through outer wall 25a, as illustrated in FIG. 2, so that electric leads 27 may be passed through the annular space (longitudinal passage 23) between outer wall 25a and inner wall 25b for connection with impedance spectrometer system 30. In other embodiments, electrodes 26 are surface mounted to the inflatable section 24 with wires extending through the outer wall. Beneath the electrodes or at other regions of the introducer 30, e.g. at the proximal end, data storage capabilities can be provided so that measurements may be analyzed after the introducer is retrieved. The electrodes may also be connected to a wireless transmitter to gather information while the introducer is taking readings in vivo for transmission to an external wireless receiver.

Electrodes 26 are spaced apart and around the circumference of inflatable section 24. The plurality of electrodes 26 are spaced, patterned, and positioned, in any geometry or conductivity distribution within the purview of those skilled in the art to optimize the voltage difference between normal and abnormal tissue. In other embodiments, electrodes 26 are spaced radially, longitudinally, spirally, or in combinations thereof. In a like manner, electrodes 26 may be any shape or size to optimize reading accuracy and/or ability.

Introducer 20 is preferably formed of a flexible and/or elastomeric material to facilitate advancement through the lumen to access the measurement site. Inflatable section 24 may also be formed of any suitable elastomeric material. The material is capable of inflating while maintaining the integrity of introducer 20 and is compatible with distention fluid. Distention fluid may be a gas, liquid, or the like. In some embodiments, inflatable section 24 contains folds which expand with the addition of distention fluid, thereby increasing the surface area of inflatable section 24. In other embodiments, inflatable section 24 is formed from a stretch material. Other techniques for forming the inflatable section, as well as the selection of materials having high elasticity/low tensile modulus, are within the purview of those skilled in the art. As shown in FIG. 4, inflatable section 24 expands to a diameter "D1" larger than the diameter "D" of introducer 20.

Referring now to FIGS. 4 and 5, electrodes 26 of inflatable section 24 of introducer 20 may be selectively utilized to measure tissue impedance. FIG. 5 illustrates electrodes 26 alternately connected to a four contact system including two signal lines and two measurement lines. Two outer electrodes 26a and 26d are attached to signal lines, $V_1$ and $V_2$, respectively, and two inner electrodes 26b and 26c are attached to measurement lines, $M_1$ and $M_2$, respectively. Inner electrodes 26b and 26c are spaced between and in alignment with outer electrodes 26a and 26d, which are in spaced relation to each other. Outer electrodes 26a and 26d transmit an electrical signal to tissue via impedance spectrometer system 30 and inner electrodes 26b and 26c measure the resulting potential which is processed by impedance spectrometer 30.

To alternate between different electrodes, shaft 40 may extend through introducer 20 to shift the electrode contact system clockwise or counterclockwise around the circumference of the tissue. Alternatively, as illustrated in FIG. 5, an external control, such as commutator 50, may be used to alternate the function of each electrode by shifting the contacts of the system such that no physical movement of inflatable section 24 is required to take measurements around the tissue.

FIG. 6 illustrates electrodes 26 alternatively connected to a three contact system including a signal line, a measurement line, and a combined (common) signal and measurement line. Outer electrode 26e is attached to a signal line, V, and inner electrode 26f is attached to a measurement line, M. Outer electrode 26g functions as both a signal and a measurement line. Impedance, therefore, is measured across electrodes 26e and 26f as well as at the site of electrode 26g.

It is envisioned that other electrode contact configurations may be used with the tissue monitoring system of the present disclosure, the systems including different electrode relationships for measuring transfer and/or site impedance.

Impedance spectrometer 30 includes the components necessary to allow energy to be applied to tissue by way of electrodes 26 on inflatable section 24 of introducer 20, to receive the spectral response of the tissue from the energy applied, and to process the readings received to get a measure of the state of the tissue. The state of the tissue can be quantified by measuring it against normal tissue or against an algorithm trained to measure tissue properties or conditions, such as ischemia. Such impedance spectrometer systems and processing methods are known to those skilled in the art and include, for example, U.S. Pat. No. 5,807,272 to Kun et al. and U.S. Pat. No. 5,454,377 to Dzwonczyk et al., the entireties of which are hereby incorporated by reference.

To use the tissue monitoring system of the present disclosure, the introducer is inserted proximal to a section of tissue, such as the gastrointestinal tract (see e.g. FIG. 1). The inflatable section is inflated with a distention fluid, such as pressurized air. The inflatable section expands until the plurality of electrodes on the inflatable section is in communication with the surface of the tissue. The desired subset of electrodes, based on the electrode contact system utilized, is selected to take a reading. In certain embodiments, multiple subsets of electrodes may be utilized at the same time to take multiple measurements about the tissue. In other embodiments, a multiplexer may be used for selection of electrodes for measurement readings.

For example, in a four contact system, four adjacent electrodes are used to take a reading. Two electrodes, spaced apart by two inner electrodes, are connected to an energy source of the impedance spectrometer system. The spectrometer system causes the electrodes to inject a constant voltage or electrical signal, into the tissue at a series of different frequencies. The spacing of the electrodes allows the inner electrodes to measure the voltage drop between themselves as a result of the electrical signal at the outer electrodes. The voltage measured by the inner electrodes provides a measurement of the impedance of the two inner electrodes, and thereby of the impedance in the tissue. These readings are received by the inner electrodes or sent to an output circuit of the spectrometer system. In some embodiments, the readings may be sent to a second spectrometer such that the first spectrometer is dedicated to current input and the second spectrometer for output and signal processing.

The measurements produced contain information about the electrical characteristics of the tissue, such as impedance and conductivity values, which in turn impart information about the structural and metabolic status of the tissue which can be used to quantify the level of damage in the tissue.

Once a reading has been taken, the four contact system would then be shifted one electrode clockwise or counterclockwise so that each contact on the four contact system would be connected to the electrode adjacent to the electrode it was connected to previously. Readings would then be taken as described above. This would preferably be repeated until the entire circumference of the tissue has been characterized. This configuration would provide information about the circumferential segment encompassed by the electrodes.

In further embodiments, anastomosed tissue is characterized by the present method. These measurements can be taken on tissue both distal and proximal to the staple line by axial movement of the introducer. In the alternate embodiment of FIG. 7, the readings can be taken at the same time by use of two inflatable sections 34 on the introducer 30. Both inflatable sections 34 are spread from distalmost end 32 of distal portion 31. Electrodes 36 are positioned circumferentially on inflatable sections 34. Electrode leads can be passed through longitudinal passageway 33.

It will be understood that various modifications may be made to the embodiments disclosed herein. Therefore, the above description should not be construed as limiting, but merely as an exemplification of the embodiments. Those skilled in the art will envision other modifications within the scope and spirit of the present disclosure. Such modifications and variations are intended to come within the scope of the following claims.

What is claimed is:

1. A surgical tissue monitoring system comprising:
   an introducer having a first inflatable section and a first plurality of electrodes disposed about the first inflatable section, and a second inflatable section axially spaced from the first inflatable section, the first and second inflatable sections defining a gap therebetween along the introducer, the second inflatable section having a second plurality of electrodes disposed about the second inflatable section; and
   an electrode contact system comprising at least one signal line and at least one measurement line, wherein electrodes of each of the first and second plurality of electrodes are alternatively connected to the at least one signal line and the at least one measurement line for taking readings about a circumferential segment of tissue encompassed by the electrodes.

2. The tissue monitoring system of claim 1, wherein the electrode contact system is a four contact system comprising two signal lines peripheral to two measurement lines.

3. The tissue monitoring system of claim 1, wherein the electrode contact system is a three contact system comprising a signal line, a measurement line, and a common signal and measurement line.

4. The tissue monitoring system of claim 1, further comprising a spectrometer for applying energy to the tissue.

5. The tissue monitoring system of claim 4, further comprising a second spectrometer for receiving a response from the tissue.

6. The tissue monitoring system of claim 1, further comprising a rotating shaft for alternating placement of the electrodes.

7. The tissue monitoring system of claim 1, further comprising an external control for alternating functioning of the electrodes by shifting contacts of the electrode contact system.

8. The tissue monitoring system of claim 1, further comprising a shaft extending through the introducer, the shaft being rotatable with respect to the introducer to shift the electrode contact system clockwise or counterclockwise around the circumferential segment of tissue.

9. The tissue monitoring system of claim 1, wherein contacts of the electrode contact system encompass a subset of the electrodes and are configured and adapted to shift and encompass a different subset of the electrodes.

* * * * *